(12) United States Patent  
Albertorio

(10) Patent No.: US 9,095,641 B2
(45) Date of Patent: Aug. 4, 2015

(54) HYBRID POLYMER/METAL PLUG FOR TREATING CHONDRAL DEFECTS

(75) Inventor: Ricardo Albertorio, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 12/976,581

(22) Filed: Dec. 22, 2010

(65) Prior Publication Data

US 2011/0153028 A1 Jun. 23, 2011

Related U.S. Application Data

(60) Provisional application No. 61/289,320, filed on Dec. 22, 2009.

(51) Int. Cl.
| | |
|---|---|
| *A61F 2/38* | (2006.01) |
| *A61L 27/56* | (2006.01) |
| *A61F 2/30* | (2006.01) |
| *A61L 27/42* | (2006.01) |
| *A61L 27/48* | (2006.01) |
| *B29C 45/14* | (2006.01) |

(52) U.S. Cl.
CPC .............. *A61L 27/56* (2013.01); *A61F 2/30756* (2013.01); *A61L 27/427* (2013.01); *A61L 27/48* (2013.01); *B29C 45/14* (2013.01); *A61F 2002/30013* (2013.01); *A61F 2250/0024* (2013.01); *A61L 2430/06* (2013.01); *B29C 2045/14327* (2013.01)

(58) Field of Classification Search
CPC ............ A61F 2002/30971; A61F 2002/30766; A61F 2/38; A61F 2/3872; A61F 2/30756; A61F 2002/30013; A61F 2250/0024; B29C 2045/14327; B29C 45/14

USPC ....................................................... 623/14, 12
See application file for complete search history.

(56) References Cited

U.S. PATENT DOCUMENTS

| | | | | |
|---|---|---|---|---|
| 5,879,387 | A | * | 3/1999 | Jones et al. ................. 623/18.11 |
| 6,632,246 | B1 | * | 10/2003 | Simon et al. ................ 623/14.12 |
| 7,264,634 | B2 | | 9/2007 | Schmieding |
| 7,901,457 | B2 | | 3/2011 | Truncale et al. |
| 2001/0039455 | A1 | | 11/2001 | Simon et al. |
| 2003/0055502 | A1 | * | 3/2003 | Lang et al. ................. 623/16.11 |
| 2004/0034437 | A1 | | 2/2004 | Schmieding |
| 2004/0098133 | A1 | * | 5/2004 | Carignan et al. ............ 623/20.35 |
| 2007/0142914 | A1 | * | 6/2007 | Jones et al. ................. 623/14.13 |
| 2007/0179607 | A1 | * | 8/2007 | Hodorek et al. ............ 623/14.12 |
| 2007/0219638 | A1 | * | 9/2007 | Jones et al. ................. 623/19.11 |
| 2009/0164014 | A1 | | 6/2009 | Liljensten et al. |
| 2009/0259313 | A1 | * | 10/2009 | Elsner et al. ............... 623/14.12 |

FOREIGN PATENT DOCUMENTS

WO  WO 2009/092082 A2  7/2009

* cited by examiner

*Primary Examiner* — Randy Shay
(74) *Attorney, Agent, or Firm* — Dickstein Shapiro LLP

(57) ABSTRACT

Osteochondral implants for repair of chondral defects and providing bone fixation through bone ongrowth and/or ingrowth. The implant is provided with a base allowing for bone ongrowth and/or ingrowth and a top attached to the base, the top being formed of a material having a compressive resistance similar to that of the cartilage. The material of the top is polycarbonate urethane, for example. The base may comprise a porous substrate for bony ingrowth formed of metal or PEEK and having a pattern porosity about similar to the porosity of cancellous bone. One side of the top attaches to the base for stability, and the other side of the top forms a surface for articulating with the opposing cartilage surface of the joint.

2 Claims, 4 Drawing Sheets

HYBRID POLYMER/METAL PLUG FOR TREATING CHONDRAL DEFECTS

CROSS-REFERENCE TO RELATED APPLICATIONS

This application claims the benefit of U.S. Provisional Application No. 61/289,320, filed Dec. 22, 2009, the entire disclosure of which is incorporated by reference herein.

FIELD OF THE INVENTION

The present invention relates to surgical systems for treating osteochondritis dissecans.

DESCRIPTION OF THE RELATED ART

Osteochondritis dissecans is a disease of the cartilage. The cartilage develops blemishes, fissures or large full-thickness defects as a result of ligament damage or isolated pathology. If left untreated, the defects can lead to enlargement of the defect and ultimately an advancing arthritic condition. These defects are referred to as chondral or focal defects.

Chondral defects can be treated by autograft or allograft transplantation of bone cores in the knee. Concerns of donor site morbidity when using allograft transplants, or tissue viability, rejection, and transmission of infection when using allograft tissue has prompted development of artificial alternatives for partial articular surface replacement. Recently, synthetic implants have been developed for treatment of these defects. One example of a synthetic implant is manufactured by Salumedica of Atlanta, Ga. using a hydrogel material known as Salubria™. Another example of a synthetic implant is manufactured by Arthrosurface and uses a combination of metal and ultra high weight polyethylene. The problems associated with these synthetic implants include poor bone anchorage and/or excessive wear against opposing surfaces. Accordingly, it would be desirable to provide a synthetic implant for repairing chondral defects that (i) anchors to bone through bone ongrowth and/or ingrowth, (ii) closely matches the compliance of human tissue, (iii) is wear resistant, and (iv) does not damage the opposing natural cartilage surface.

SUMMARY OF THE INVENTION

The present invention provides surgical systems for treatment of osteochondritis dissecans. The invention provides a novel implant that repairs chondral defects while providing optimal anchoring to bone, wear resistance, compressive resistance closely matching that of human tissue, and preservation of the opposing cartilage surface.

The implant has a porous surface for biologic fixation through bony ongrowth and/or ingrowth. The implant also includes an articulating surface providing better wear properties against opposing cartilage than metal or rigid polymer articulating surfaces. The implant can be implanted using known techniques and existing instrumentation.

These and other features and advantages of the invention will be more apparent from the following detailed description that is provided in connection with the accompanying drawings and illustrated exemplary embodiments of the invention.

DETAILED DESCRIPTION OF THE PREFERRED EMBODIMENTS

The present invention provides an implant for treatment of chondral defects. The novel implant allows for repair of chondral defects without the need to harvest autograft or allograft implants, while providing bone fixation through bone ongrowth and/or ingrowth, minimizing wear, closely matching the compliance of human tissue, and preserving the opposing cartilage surface.

In an exemplary embodiment, the implant includes a base allowing for bone ongrowth and/or ingrowth and a top attached to the base, the top being formed of a material having a compressive resistance similar to that of the cartilage. In exemplary embodiments, the material of the top is a polymer (such as polycarbonate urethane, for example) that has a modulus of elasticity about equal to that of the cartilage. The base may comprise a porous substrate for bony ingrowth formed of metal or PEEK and having a pattern porosity about similar to the porosity of cancellous bone. One side of the top attaches to the base for stability, and the other side of the top forms a surface for articulating with the opposing cartilage surface of the joint.

Figure 1A:
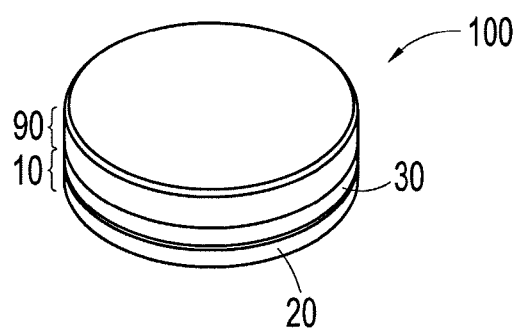
FIG. 1A illustrates a perspective view of an implant for repairing a chondral defect, according to an exemplary embodiment of the present invention.
Figure 1C:
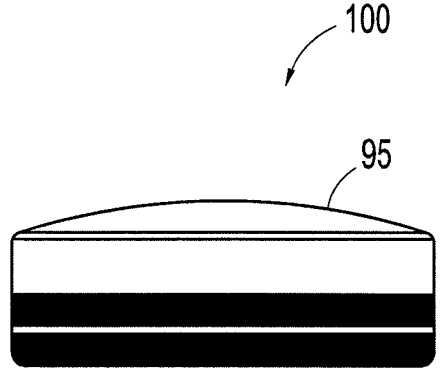
FIG. 1C illustrates a front view of the implant of FIG. 1A.
Figure 1B:
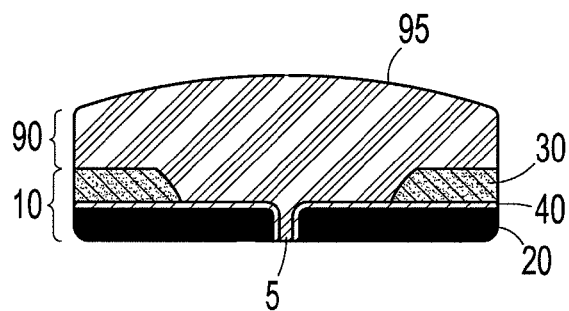
FIG. 1B illustrates a crossectional view of the implant of FIG. 1A.
Figure 1D:
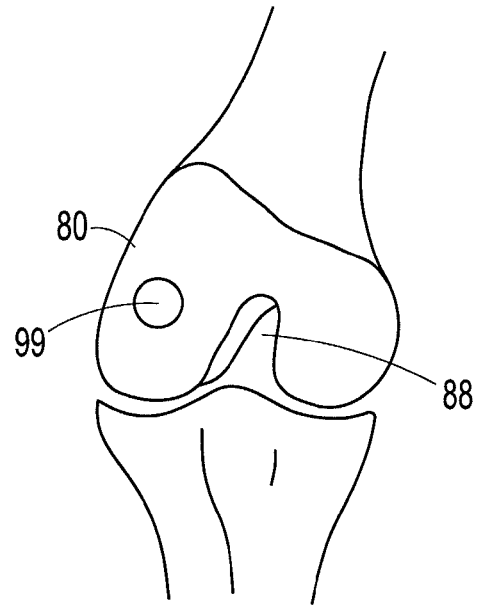
FIG. 1D illustrates a chondral defect in the knee.

Referring now to the drawings, where like elements are designated by like reference numerals, FIGS. 1A-C and FIG. 4 illustrate an exemplary implant 100 of the present invention for treatment of a chondral defect. An example of a chondral defect 99 in a knee is illustrated in FIG. 1D. The implant includes a base 10 and a top 90. The top 90 includes an articulating surface 95 for articulating with opposing surface and load sharing with the surrounding cartilage upon implantation. The top 90 may be formed of a polymer having similar compressive resistance as that of the cartilage. The base 10 provides bone fixation through bony ongrowth and/or ingrowth to create a stable repair to the defect. Preferably a number of implants are provided to a surgeon in varying shapes and sizes to accommodate anatomic and lesion geometry.

The base 10 is adapted to be implanted in or on bone. The base 10 is configured to be secured or anchored to the bone and is preferably customized to promote bone ongrowth and/ or ingrowth. In one embodiment, the base may include a region of porosity for bone ingrowth. The region of porosity interfaces with the bone when the implant is implanted into the patient. When the implant is implanted in the patient's bone, the bone will grow into the pores resulting in fixation of the implant to the bone. The base may be formed from a porous substrate made of material such as biocompatible metal (e.g., a cobalt chromium alloy, a titanium alloy, tantalum or stainless steel); a carbonaceous material, PEEK, ceramic or bone, or combination of these materials. The surface roughness of the substrate is configured to allow bony ongrowth, and/or the porosity of the substrate is sized to allow for bony ingrowth.

Base 10 may have differing layers of porosity. For example, the bottom layer 20 may have a porosity suitable for bone fixation such that after implantation bone ingrowth fixes the base of the implant. A second or top layer 30 of the base 10 may have a porosity differing from the bottom layer 20. The porosity of the top layer 30 may provide for inflow of the polymer into the base 10 for a more solid interface between the polymer and the base. This could also be accomplished using a substrate having a gradient porosity. An additional barrier layer 40 may be formed between a portion of the top layer 30 and bottom layer 20 of the base to prevent the polymer from penetrating into the pores of the bottom layer intended for bone ingrowth. An opening 5 may be provided in the bottom layer 20 and the barrier layer 40 to allow for injection molding of the polymer. In a preferred embodiment, the substrate is made from titanium having a porosity that is typical of cancellous bone found in the region of implantation.

In an alternate embodiment, the base may optionally include a coating. The coating may be configured for bone ongrowth and/or ingowth. The coating is applied to a solid base so that the coating is disposed between the base and the bone of the patient. The coating may be any known coating suitable for promoting bone ongrowth and/or ingrowth. For example, the coating may be a porous coating, such as a sintered bead coating, a mesh coating, or a plasma spray. Additionally, or alternately, the coating may be bioactive, such as hydroxyapatite.

Figure 3A:
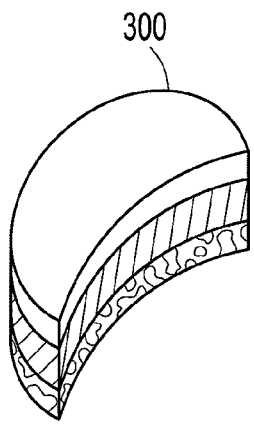
FIGS. 3A-C illustrate various shapes and sizes of the implant of the present invention.
Figure 3B:
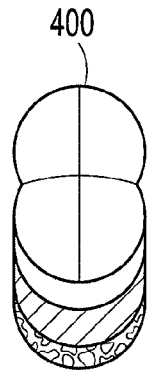
Figure 3C:
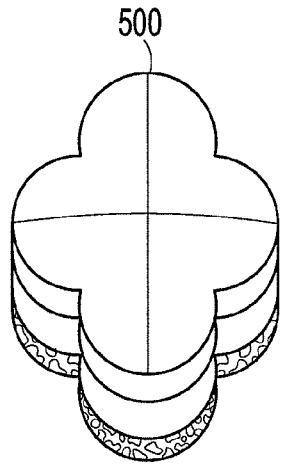
Figure 4:
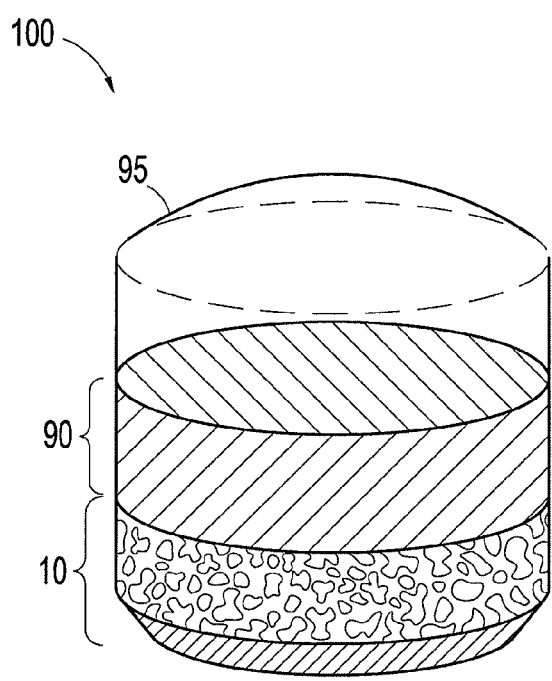
FIG. 4 illustrates a schematic view of the implant of FIG. 1.

A polymer is attached to the base 10 to create a top 90 having an articulating surface 95 on the implant. The polymer may be injection molded through the base of the implant during manufacture. The polymer has a compressive resistance similar to that of the surrounding cartilage to provide for load-sharing between the implant and the native surrounding cartilage. An example of a polymer having such properties is polycarbonate urethane. The polymer layer matches closely the depth of the surrounding cartilage of the defect. In a preferred embodiment, the polymer layer of the implant is 2-7 mm or approximately one third the thickness of the total implant. The articulating surface may be concave, convex, or a freeform geometry to more closely match the opposing anatomic geometry. In a longitudinal cross-sectional view, the articulating surface may have a simple radius of curvature or may have a more complex radius of curvature, for example partially elliptical, lunate or other asymmetric shape. As illustrated in FIGS. 3A-C, implants 300, 400, 500 can be provided in a variety of sizes, shapes, and curvatures to allow for mosaicplasty for treating defects of irregular shapes and curvatures.

A kit containing implants or temporary templates of various shapes, sizes and curvatures, for repair of irregular chondral defects may be provided to the surgeon. In an exemplary embodiment, the implant is cylindrical having diameter between 4-20 mm and a height between 4-20 mm.

Figure 2:
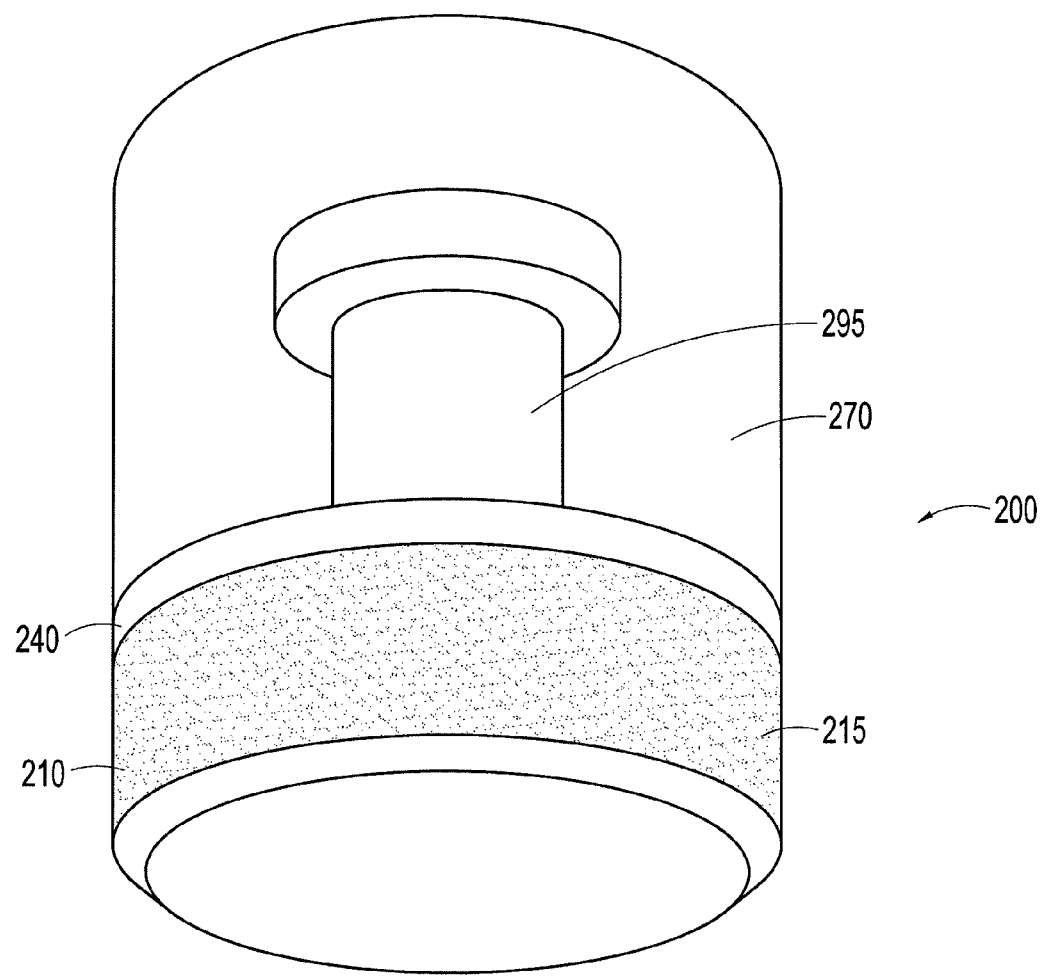
FIG. 2 illustrates another exemplary embodiment of an implant of the present invention.

In an alternate embodiment illustrated in FIG. 2, the implant 200 includes a base 210, a top 270 and a barrier layer 240. The base 210 may have additional features such as undercuts or protrusions 295 such as a stem or rod formed on one side of the base. The protrusion 295 allows the polymer to permanently attach to the substrate of the base 210. The base 210 may also have a porous coating 215 to facilitate bone ongrowth and/or ingrowth. Alternately, an adhesive could be used to bond or attach the polymer to the base.

The present invention also provides methods of treating chondral defects by providing hybrid plugs that confer optimal anchoring to the bone. The hybrid plug of the present invention is provided with a porous region (having a pattern porosity about similar to the pattern porosity of the bone at the chondral defect site) that allows biological fixation through bone ongrowth and/or ingrowth. The hybrid plugs of the present invention may be implanted/inserted using known OATS™ (Osteochondral Autograft Transfer System) techniques and instrumentation, such as the ones described and detailed in U.S. Pat. No. 5,919,196 to Bobic et al. and in U.S. Pat. No. 7,591,820 to Schmieding et al., for example, the disclosures of both of which are incorporated in their entirety herewith.

A method of treating a chondral defect in a joint having articular cartilage and subchondral bone comprises inter alia the steps of: (i) preparing an implant recipient site within the joint; (ii) providing a hybrid osteochondral plug of the present invention, such as the implant 100 described above (comprising a base having a porous region with a pattern porosity similar to the pattern porosity of bone at the chondral defect, and a top formed of polymer having similar compressive resistance as that of cartilage from opposing natural cartilage surface); (iii) inserting the plug 100 into the implant recipient site so that the porous region of the base interfaces with the bone at the recipient site; and (iv) anchoring the plug to the bone, through bone ongrowth and/or ingrowth through the pores of the porous region of the base, to provide bone fixation and create a stable repair to the chondral defect.

Figure 5:
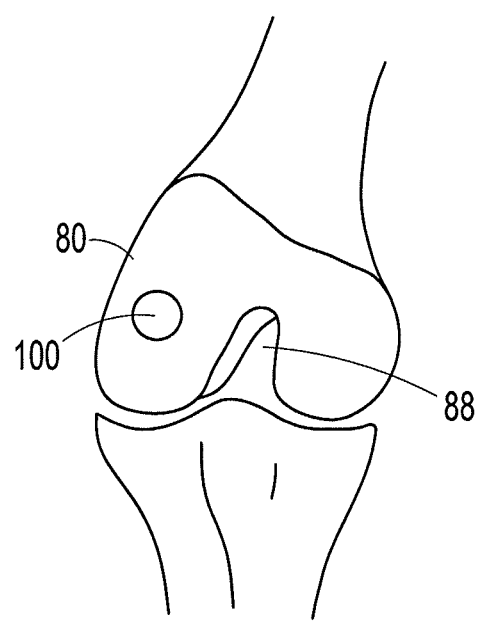
FIG. 5 illustrates the implant of FIG. 1 inserted into the chondral defect in the knee of FIG. 1D.

FIG. 5 illustrates hybrid osteochondral plug 100 of the present invention inserted into recipient site 99 (FIG. 1D) of femoral condyle 80 of knee joint 88. Hybrid osteochondral plug 100 (preferably formed of metal such as titanium or PEEK) is inserted so that porous region 10 of the base interfaces the bone of the chondral defect. As a result of the pattern porosity of the region 10 being about similar to that of the bone of the recipient site 99, the hybrid osteochondral plug 100 will be anchored to the bone through bone ongrowth and/or ingrowth through the pores of the porous region 10, providing increased bone fixation and creating a stable repair to the chondral defect. The top articulating surface 95 of the hybrid osteochondral plug 100 is preferably formed of a polymer (such as polycarbonate urethane) having a modulus of elasticity about equal to that of cartilage (i.e., a compressive resistance similar to that of the cartilage), providing therefore a close match of the compliance of human tissue and preserving the opposing cartilage surface.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A method of treating a chondral defect in a joint having articular cartilage and subchondral bone, comprising the steps of:
preparing an implant recipient site within the articular cartilage of the joint;
providing a hybrid osteochondral plug comprising a base having a porous region with pores for bone ingrowth formed of titanium and with a pattern porosity similar to the pattern porosity of cancellous bone at the chondral defect, a bather layer over and in contact with the base, and a top over and in contact with the barrier layer, the top being formed of polymer comprising polycarbonate urethane having similar compressive resistance as that of cartilage from opposing natural cartilage surface, the top formed of the polymer having a thickness which is about one third a total thickness of the hybrid osteochondral plug and matches a depth of surrounding articular cartilage of the chondral defect, wherein the hybrid osteochondral plug is formed by providing an opening in the base and in the barrier layer, the barrier layer extending onto sides of the base facing the opening, and then injecting molding a polymer through the opening in the base to permanently attach the polymer to the base including the sides of the base facing the opening, so that both the polymer and the barrier layer are disposed in the opening in the base, the barrier layer preventing the polymer from penetrating into the pores of the porous region of the base during the injection molding;

inserting the plug into the implant recipient site so that the porous region of the base and the opening in the base contact the cancellous bone and interface with the cancellous bone, allowing bone to grow into the pores of the porous region; and anchoring the plug to the cancellous bone through bone ongrowth and/or ingrowth through the porous region of the base to provide bone fixation and create a stable repair to the chondral defect.

2. The method of claim 1, wherein the ongrowth and/or ingrowth through the porous region of the base results in fixation of the hybrid osteochondral plug to the bone.

\* \* \* \* \*